(12) United States Patent
Aguilar et al.

(10) Patent No.: US 6,525,195 B1
(45) Date of Patent: Feb. 25, 2003

(54) METHOD FOR OBTAINING POLYMORPH A FROM DOXAZOSINE MESYLATE

(75) Inventors: Carmen Arnalot I Aguilar, Girona (ES); Jordi Bosch I Lladó, Girona (ES); Ma Carmen Onrubia Miguel, Barcelona (ES)

(73) Assignee: Medichem, S.A., Barcelona (ES)

( * ) Notice: Subject to any disclaimer, the term of this patent is extended or adjusted under 35 U.S.C. 154(b) by 0 days.

(21) Appl. No.: 09/913,778

(22) PCT Filed: Mar. 13, 2000

(86) PCT No.: PCT/ES00/00086

§ 371 (c)(1),
(2), (4) Date: Aug. 14, 2001

(87) PCT Pub. No.: WO00/55157

PCT Pub. Date: Sep. 21, 2000

(30) Foreign Application Priority Data

Mar. 16, 1999 (ES) .............................................. 9900535

(51) Int. Cl.[7] ............................................. C07D 405/14
(52) U.S. Cl. ....................................................... 544/291
(58) Field of Search ......................................... 544/291

(56) References Cited

U.S. PATENT DOCUMENTS 4,188,390 A    2/1980    Campbell
6,130,218 A   10/2000    Mörsdor et al.
6,133,269 A   10/2000    Mörsdor et al.
6,140,334 A   10/2000    Mörsdor et al.

FOREIGN PATENT DOCUMENTS

| EP | 849266 A1 * | 12/1996 |
| EP | 0 848 001 A1 | 6/1998 |
| WO | WO 96/39406 | 12/1996 |
| WO | WO 99/35143 | 7/1999 |

OTHER PUBLICATIONS

Chem Abstract Plus 1997–724496, M. Groman, et al., in "Farm. Vestn" 1997, 48:292–293.

Chem Abstract 124–325182, Xu Liying, et al., in "Zongguo Yaowu Huaxue Zazhi", 1995, vol. 5, part 4, pp. 266–270.

* cited by examiner

*Primary Examiner*—Emily Bernhardt
(74) *Attorney, Agent, or Firm*—Scully, Scott, Murphy & Presser

(57) ABSTRACT

The invention discloses a process for the preparation of the polymorh A of doxazosin meylate, consisting essentially of reacting doxazosin base with methanesulfonic acid in a mixture of solvents containing an alcohol and a chlorinated solvent, subsequently removing the chlorinated solvent by distillation and precipitating the desired product in an alcohol, after heating the suspension formed to the reflux temperature of the solvent.

15 Claims, 3 Drawing Sheets

METHOD FOR OBTAINING POLYMORPH A FROM DOXAZOSINE MESYLATE

FIELD OF THE ART

This invention relates to a process for the preparation of the polymorph A of doxazosin mesylate. This polymorph is crystalline and is named Form A.

PRIOR ART REFERENCE

Doxazosin is the generic name (INN) of 1-(4-amino-6,7-dimethoxy-2-quinazolinyl)-4-[(2,3-dihydro-1,4-benzodioxin-2-yl)carbonyl]-piperazine, of formula

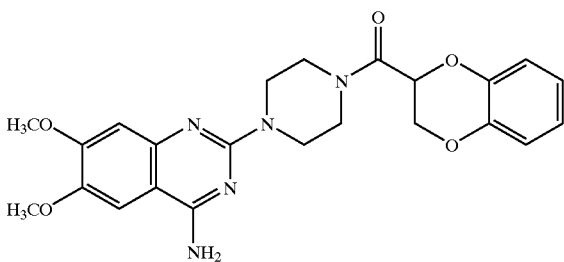

which is used as described in The Merck Index, article 3422 of the XI Edition (1989) and article 3489 of the XII Edition (1996), as the equimolar salt thereof with methanesulfonic acid (monomethanesulfate or monomesylate), as a antihypertensive drug marketed under the following brand names, among others: Aldafil®, Cardura®, Carduran®, Diblocin®, Supressin®, etc.

U.S. Pat. No. 4,188,390, of which ES-A474 805 is the equivalent, describes both doxazosin and, generically, the pharmaceutical salts thereof and although doxazosin mesylate is not explicitly described in these documents, it is indicated therein that the pharmaceutical salts may include the addition salts with sulfonic acids.

In the article published by Xu Liying et al., in *Zongguo Yaowu Huaxue Zazhi*, 1995, Vol. 5, part 4, pages 266–270, summarized in Chemical Abstracts, ref. CA 124:325182, there is described for the first time the crystalline polymorphism proper to doxazosin mesylate. Three polymorphs, designated A, B and C are identified in the above article, with the use of differential thermal analysis, infra red spectroscopy and X-ray diffraction techniques, although extremely superficial instructions are given for the preparation thereof, limited to stating that the form A is prepared by recrystallization of the commercial product in ethanol. It should be pointed out that the above article speaks of doxazosin, without specifying that it is a question of the mesylate thereof, although it is clearly explained therein that the "doxazosin" used is the commercial product used for the treatment of high blood pressure, which allows it to be deduced without any doubt that the study described in the article relates to doxazosin mesylate, which is the only doxazosin salt which has been marketed as a pharmaceutical up to date.

Subsequently, M. Grcman et al., in *Farm. Vestn* 1997, 48:292–293 also described up to five different crystalline polymorphs of doxazosin mesylate, although with much less precision and data than in the Xu Liying et al. article, in spite of which it seems quite probable that the polymorph called A in the Grcman article is the same as the polymorph A described in the Xu Liying article. The Grcman article offers still fewer details on the processes for preparing the different crystalline polymorphs of doxazosin mesylate, since the authors go no further than stating that all are prepared by crystallization.

European patent applications EP-A-0 848 001, EP-A-0 849 264 and EP-A-0 849 265 disclose three different crystalline polymorphs of doxazosin mesylate, as well as processes for the preparation thereof, but none of them coincides with the polymorph A described by Xu Liying et al.

Finally, European patent application EP-A-0 849 266 discloses a crystalline polymorph of doxazosin mesylate, which is designated Form III in the said application, and which is characterized mainly by the 2θ diffraction angles in the X-ray powder diffractogram. If the infra red spectrum, the 2θ diffraction angles and the complete X-ray powder diffractogram described in EP-A-0 849 266 for the so-called Form III of doxazosin mesylate are compared with the same data given in the Xu Liying article for polymorph A, the obvious conclusion is reached that the so-called Form III is in reality the Form A of doxazosin mesylate previously described by Xu Liying et al.

The said EP-A-0 849 266 also discloses a process for the preparation of the said Form III of doxazosin mesylate consisting, in the essential aspects thereof, of the following steps:

(a) starting out from doxazosin base and reacting it with acetic acid, to form the acetate salt dissolved in an organic solvent as intermediate, (b) reacting the thus obtained solution with methanesulfonic acid, (c) crystallizing the product at reflux temperature of the solvent and removing the adduct formed by filtration, (d) adding the moist adduct to a low molecular weight alcohol and boiling under reflux for a certain time, and (e) cooling the thus obtained solution and collecting the product crystals by filtration.

As will be observed, it is a complex, time-consuming process which requires the prior formation of a salt other than the doxazosin mesylate, i.e., the acetate, to displace it subsequently with the methanesulfonic acid.

There remains, therefore, the need to have simpler, cheaper alternative processes allowing the industrial preparation of Form A of doxazosin mesylate.

OBJECT OF THE INVENTION

The object of the present invention is a process for the preparation of Form A of doxazosin mesylate, the industrial application of which is easy and cheap, starting out from easily industrially accessible intermediates and without the need for preparing intermediate salts other than the mesylate.

DESCRIPTION OF THE INVENTION

Figure 1:
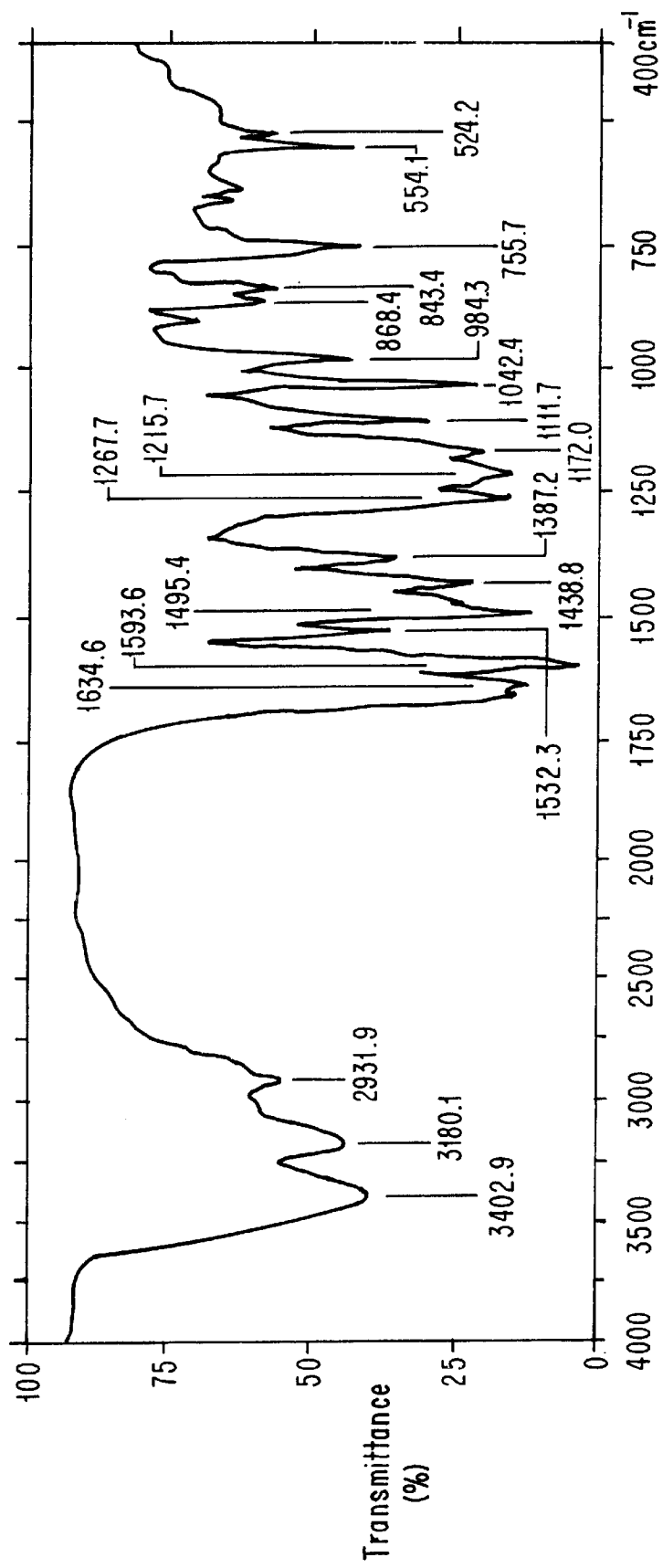
FIG. 1 shows the infra red spectrum described for Form A of doxazosin mesylate in the above mentioned Xu Liying et al. article.

The authors of the present invention have found that the Form A crystalline polymorph of doxazosin mesylate may be prepared by a process characterized in that it comprises the following steps:
(i) reacting doxazosin base with methanesulfonic acid in a mixture of solvents containing a short chain $C_1$–$C_4$ alcohol and a chlorinated non-polar aliphatic solvent,
(ii) removing the chlorinated solvent from the mixture by distillation, and
(iii) adding an additional amount of a short chain $C_1$–$C_4$ alcohol and heating the suspension formed to the reflux temperature of said alcohol, followed by cooling to a temperature equal to or below 30° C. and isolating the Form A of doxazosin mesylate by filtration and drying.

The doxazosin base and the methanesulfonic acid are reacted in proportions close to stoichiometric or with a slight molar excess of methanesulfonic acid lower than 15%, preferably at a temperature below 50° C., more preferably below 30° C. and the volumetric proportions of the mixture of short chain alcohol/chlorinated solvent range from 90:10 to 10:90 (v/v), preferably from 70:30 to 30:70 (v/v) and more preferably from 60:40 to 40:60 (v/v).

Among the short chain $C_1$–$C_4$ alcohols there may be mentioned methanol, ethanol, isopropanol, n-butanol, etc., methanol being preferred.

Among the chlorinated non-polar aliphatic solvents there may be mentioned methylene chloride, chloroform, carbon tetrachloride, dichloroethane, perchloroethylene, etc., methylene chloride being preferred.

Particularly preferred is the use in step (i) of a mixture of methanol and methylene chloride at a ratio of 50:50 (v/v).

The starting doxazosin base may be prepared from doxazosin hydrochloride, which may be prepared in turn as described in U.S. Pat. No. 4,188,390, by the addition of an alkaline hydroxide, for example sodium hydroxide, in an aqueous medium, or by any other method generally known to the man of the art. Said doxazosin base, if prepared in an aqueous medium, may be used in step (i) after drying or may also be used in the moist form, with the residual water content left after filtration, in which case the solvent system for step (i) contains three components, the water being in a minor proportion, in any case less than 20 wt % of the total of the reaction mixture of said step (i).

The chlorinated solvent is removed, step (ii), by distillation of the reaction mixture from step (i), preferably at reduced pressure which allows said chlorinated solvent to be removed completely at a temperature below 25° C., more preferably below 20° C. Practice shows that it is sufficient for the above purposes to distill at a pressure below 75 mbar, preferably below 50 mbar.

It should be understood that the terms "removal of solvent" and "complete removal of solvent" are used to express that the major portion of the chlorinated solvent has been removed, it being inevitable that some amount thereof remains undistilled.

Preferably, prior to removing the chlorinated solvent, a step of filtration of the reaction mixture from step (i) may be inserted, so as to remove insoluble impurities.

The short chain alcoholic solvent of step (iii) may be selected from the group formed by, among others, methanol, ethanol, isopropanol, n-butanol, etc., methanol being the preferred one, and the suspension of the doxazosin mesylate in the alcoholic solvent is heated to reflux, with stirring, and is cooled to below 30° C., preferably to between 10° C. and 20° C. and stirring is continued for an additional period of time so that the product may finish crystallizing.

The filtering and drying conditions of the product are conventional, a drying temperature of under 70° C. being recommendable, preferably at reduced pressure.

Figure 2:
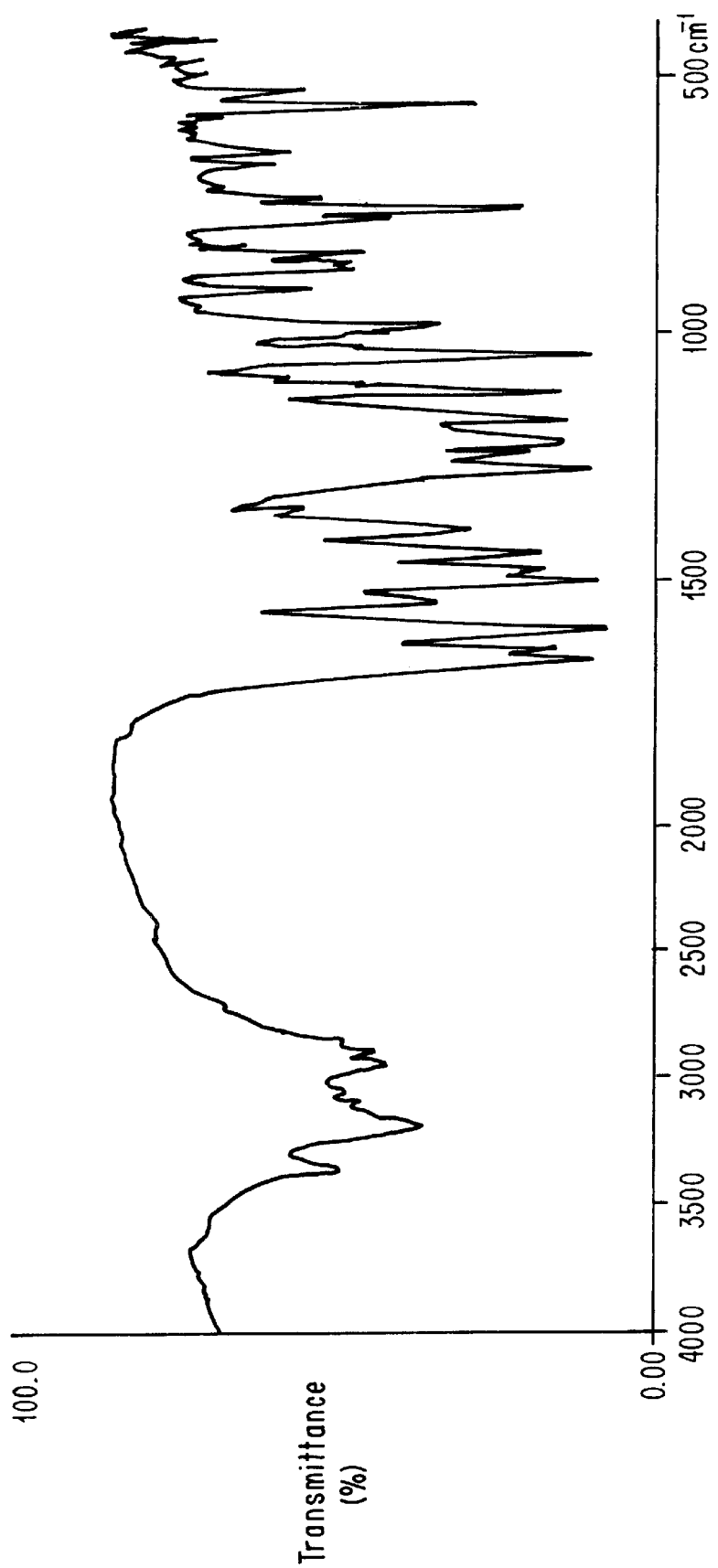
FIG. 2 shows the infra red spectrum of the Form A of doxazosin mesylate prepared by the process of the present invention.

In the above mentioned way, Form A of doxazosin mesylate is obtained with a yield of over 90%. The infra red spectrum thereof is shown in FIG. 2 and is substantially coincident with the infra red spectrum described for Form A in the above mentioned the Xu Liying et al. article, and which is shown in FIG. 1.

Figure 3:
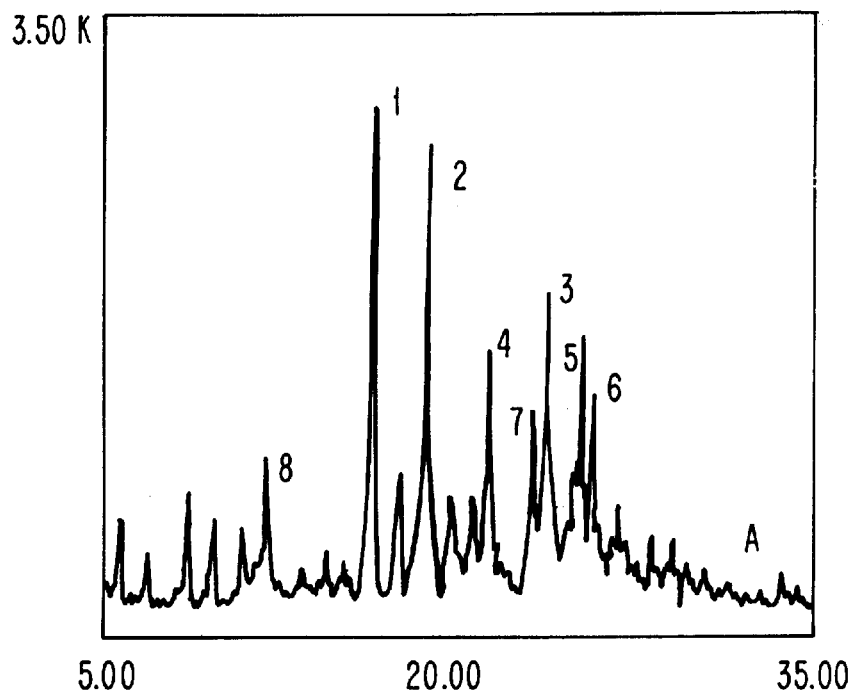
FIG. 3 is the X-ray powder diffraction diagram trace described for Form A of doxazosin mesylate in the above mentioned Xu Liying et al. article.
Figure 4:
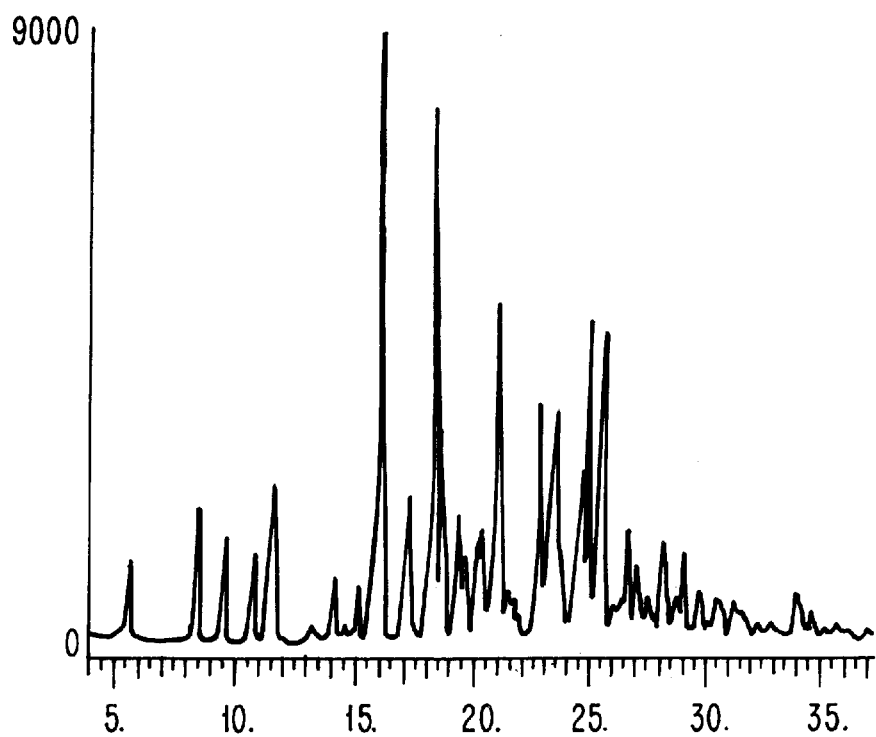
FIG. 4 is the X-ray powder diffraction diagram trace of the Form A of doxazosin mesylate prepared by the process of the present invention.

In turn, FIG. 4 shows the X-ray powder diffraction diagram trace of the product prepared with the process of the present invention and which is substantially coincident with the one described for Form A of doxazosin mesylate in the above mentioned Xu Liying et al. article, and which is shown in FIG. 3.

The method of the present invention affords considerable advantages over what has been described up to now, since it allows Form A of doxazosin mesylate to be prepared as the summit to the conventional industrial process for the preparation of doxazosin, almost directly and with very high yields, all without the need to form intermediate salts with different anions which have subsequently to be removed, with the use of accessible, economic solvents and using handling techniques which are absolutely normal in any fine chemistry industrial plant.

The following examples are given below for a better understanding of the object of this invention, but should not be construed as limitations thereof.

EXAMPLES

Example 1
Preparation of Doxazosin Base 501.2 g of doxazosin hydrochloride, prepared as described in U.S. Pat. No. 4,188,390, were suspended under stirring in 4 liters of water, followed by the addition of 41.08 g of sodium hydroxide. The thus obtained suspension was heated at 80° C. for minutes, always with stirring, and the pH thereof was checked to be between 9 and 11.

The mixture was cooled to 30° C. and the product was filtered and the filtered product was washed twice with 500 ml of water each time, to give 1063.3 g of moist doxazosin base which, after drying, gave 442.8 g of doxazosin base. Yield 95.5%.

Example 2
Preparation of Doxazosin Base

Using the method described in Example 1, but with the following amounts of reactants and solvents:

| | |
|---|---|
| Doxazosin hydrochloride | 471.68 g |
| Water (reaction) | 3775 ml |
| NaOH | 41.76 g |
| Water (washing) | 2 × 470 ml |

884 g of moist doxazosin base were obtained which, after drying, gave 432.91 g of doxazosin base. Yield 99.2%.

Example 3
Preparation of Form A of Doxazosin Mesylate 1063.1 g of water moist doxazosin base, equivalent to 442.8 g of doxazosin base (0.981 mol) were suspended under stirring in a mixture of 2214 ml of methanol and 2214 ml of methylene chloride. To the thus obtained suspension, there were added gradually over a period of 45 minutes, 69.91 ml of methanesulfonic acid (103.68 g; 1.079 mol), while holding the reaction temperature to below 26° C. The stirring was continued for a further hour at the above temperature (water content, according to K.F., 12.11 wt %), after which the thus obtained solution was filtered to remove insoluble matter. The filtered solution was distilled under a vacuum of 48–50 mbar and at an internal temperature of 15° C. to remove the methylene chloride, giving a mixture of two phases (the upper phase aqueous-methanolic and the lower phase oily) to which 2077 ml of methanol were added with stirring.

The thus obtained suspension of doxazosin mesylate was heated to reflux and thereafter cooled to a temperature ranging from 10° C. to 20° C., with stirring being continued for a further hour.

The thus obtained suspension was filtered and washed over the filter twice with 440 ml of methanol each time and after drying at 60° C. to a constant weight, 499.61 g of Forrn A of doxazosin mesylate were obtained, with a yield of 93%.

The infra red spectrum and the X-ray diffraction diagram trace of the product obtained are substantially coincident with those shown in FIGS. 2 and 4, respectively, and are also substantially coincident with those described in the Xu Liying et al. article and which are shown in FIGS. 1 and 3.

Example 4
Preparation of Form A of Doxazosin Mesylate 596.86 g of water moist doxazosin base, equivalent to 427.13 g of doxazosin base (0.946 mol) were suspended under stirring in a mixture of 2136 ml of methanol and 2136 ml of methylene chloride. To the thus obtained suspension, there were added gradually over a period of 30 minutes, 67.45 ml of methanesulfonic acid (100.3 g; 1.04 mol), while holding the reaction temperature to below 26° C. The stirring was continued for a further hour at the above temperature (water content, according to K.F., 0.33 wt %), after which the thus obtained solution was filtered to remove insoluble matter. The filtered solution was distilled under a vacuum of 48–50 mbar and at an internal temperature of 15° C. to remove the methylene chloride, giving a suspension, to which 2000 ml of methanol were added with stirring.

The thus obtained suspension of doxazosin mesylate was heated to reflux and thereafter cooled to a temperature ranging from 10° C. to 20° C., with stirring being continued for a further hour.

The thus obtained suspension was filtered and washed over the filter twice with 427 ml of methanol each time and after drying at 60° C. to a constant weight, 494.12 g of Form A of doxazosin mesylate were obtained, with a yield of 95.4%.

The infra red spectrum and the X-ray diffraction diagram trace of the product obtained are substantially coincident with those shown in FIGS. 2 and 4, respectively, and are also substantially coincident with those described in the Xu Liying et al. article and which are shown in FIGS. 1 and 3.

What is claimed is:
1. A process for the preparation of the polymorph A of doxazosin mesylate, comprising the following steps:

(i) reacting doxazosin base with methanesulfonic acid in a mixture of solvents containing a short chain $C_1$–$C_4$ alcohol and a chlorinated non-polar aliphatic solvent, (ii) removing the chlorinated solvent from the mixture by distillation, and (iii) adding an additional amount of a short chain $C_1$–$C_4$ alcohol and heating the suspension formed to the reflux temperature of said alcohol, followed by cooling to a temperature equal to or below 30° C. and isolating the Form A of doxazosin mesylate by filtration and drying.

2. The process of claim 1, wherein the doxazosin base and the methanesulfonic acid are reacted in stoichiometric proportions or with a molar excess of methanesulfonic acid of less than 15%.

3. The process of claim 1 or 2, wherein the reaction is conducted at a temperature below 50° C.

4. The process of claim 1, wherein the volumetric proportion of the mixture of short chain alcohol/chlorinated solvent is from 90:10 to 10:90 (v/v).

5. The process of claim 4, wherein the volumetric proportion of the mixture of short chain alcohol/chlorinated solvent is from 70:30 to 30:70 (v/v).

6. The process of claim 1, whein the short chain $C_1$–$C_4$ alcohol is selected from the group consisting of methanol, ethanol, isopropanol and n-butnol.

7. The process of claim 6, wherein the short chain alcohol is methanol.

8. The process of claim 1, wherein the chlorinated non-polar aliphatic solvent is selected from the group consisting of methylene chloride, chloroform, carbon tetrachloride, dichloroethane and perchloroethylene.

9. The process of claim 8, wherein the chlorinated non-polar aliphatic solvent is methylene chloride.

10. The process of claim 1, wherein the selected mixture of solvents is a mixture of methanol and methylene chloride in volumetric proportions of 50:50 (v/v).

11. The process of claim 1, wherein the removal of the chlorinated solvent in step (ii) is conducted at a reduced pressure below 75 mbar and at a temperature below 25° C.

12. The process of claim 1, wherein for step (iii) the short chain $C_1$–$C_4$ alcohol is selected from the group consisting of methanol, ethanol, isopropanol amd n-butanol.

13. The process of claim 12, wherein the selected short chain alcohol is methanol.

14. The process of claim 3, wherein the reaction is conducted at a temperature below 30° C.

15. The process of claim 5, wherein the volumetric proportion of the mixture of short chain alcohol/chlorinated solvent is from 60:40 to 40:60 (v/v).

* * * * *